(12) United States Patent
Kim et al.

(10) Patent No.: US 7,806,144 B2
(45) Date of Patent: Oct. 5, 2010

(54) FLOW RESTRICTOR FOR INFUSION SYSTEM

(75) Inventors: Kwan J. Kim, Fountain Valley, CA (US); Kokeb Tefera, Anaheim, CA (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1023 days.

(21) Appl. No.: 11/550,146

(22) Filed: Oct. 17, 2006

(65) Prior Publication Data
US 2008/0169031 A1      Jul. 17, 2008

(51) Int. Cl.
*F15D 1/04* (2006.01)
(52) U.S. Cl. .................. 138/44; 138/40; 138/141; 138/137; 604/264
(58) Field of Classification Search ............. 138/137, 138/140, 141, 40, 44; 604/264
See application file for complete search history.

(56) References Cited

U.S. PATENT DOCUMENTS

| | | | | |
|---|---|---|---|---|
| 3,561,493 A | | 2/1971 | Maillard et al. ............. 138/141 |
| 4,035,534 A | * | 7/1977 | Nyberg ..................... 428/34.9 |
| 4,211,741 A | | 7/1980 | Ostoich .................. 264/171.26 |
| 4,626,243 A | * | 12/1986 | Singh et al. ................. 604/141 |
| 4,627,844 A | | 12/1986 | Schmitt ..................... 604/264 |
| 5,318,539 A | | 6/1994 | O'Neil ....................... 604/118 |
| 5,447,672 A | | 9/1995 | O'Neil ....................... 264/166 |
| 5,932,307 A | * | 8/1999 | Ryan et al. ................. 428/36.9 |
| 6,328,716 B1 | * | 12/2001 | Qin et al. .................... 604/264 |
| 2002/0115966 A1 | | 8/2002 | Christensen et al. ........ 604/264 |
| 2004/0168723 A1 | | 9/2004 | Black .................... 137/505.35 |
| 2008/0004569 A1 | * | 1/2008 | McCrystle et al. .......... 604/104 |

FOREIGN PATENT DOCUMENTS

| | | |
|---|---|---|
| EP | 0380270 A2 | 7/2007 |
| WO | 2006/062132 | 7/2007 |

* cited by examiner

*Primary Examiner*—Patrick F Brinson
(74) *Attorney, Agent, or Firm*—K&L Gates LLP

(57) ABSTRACT

The present invention includes a disposable flow path for an infusion system for communicating between a fluid source and a patient. The flow path comprises a flow restrictor having first and second ends and defining a flow path between the ends. The flow restrictor comprises a plurality of materials, including a first material defining the flow path, which first material is substantially resistant to vapor transmission, and a second material different than the first material defining at least a portion of an outer surface of the flow restrictor. The second material is suitable for joining to other portions of the flow path.

11 Claims, 2 Drawing Sheets

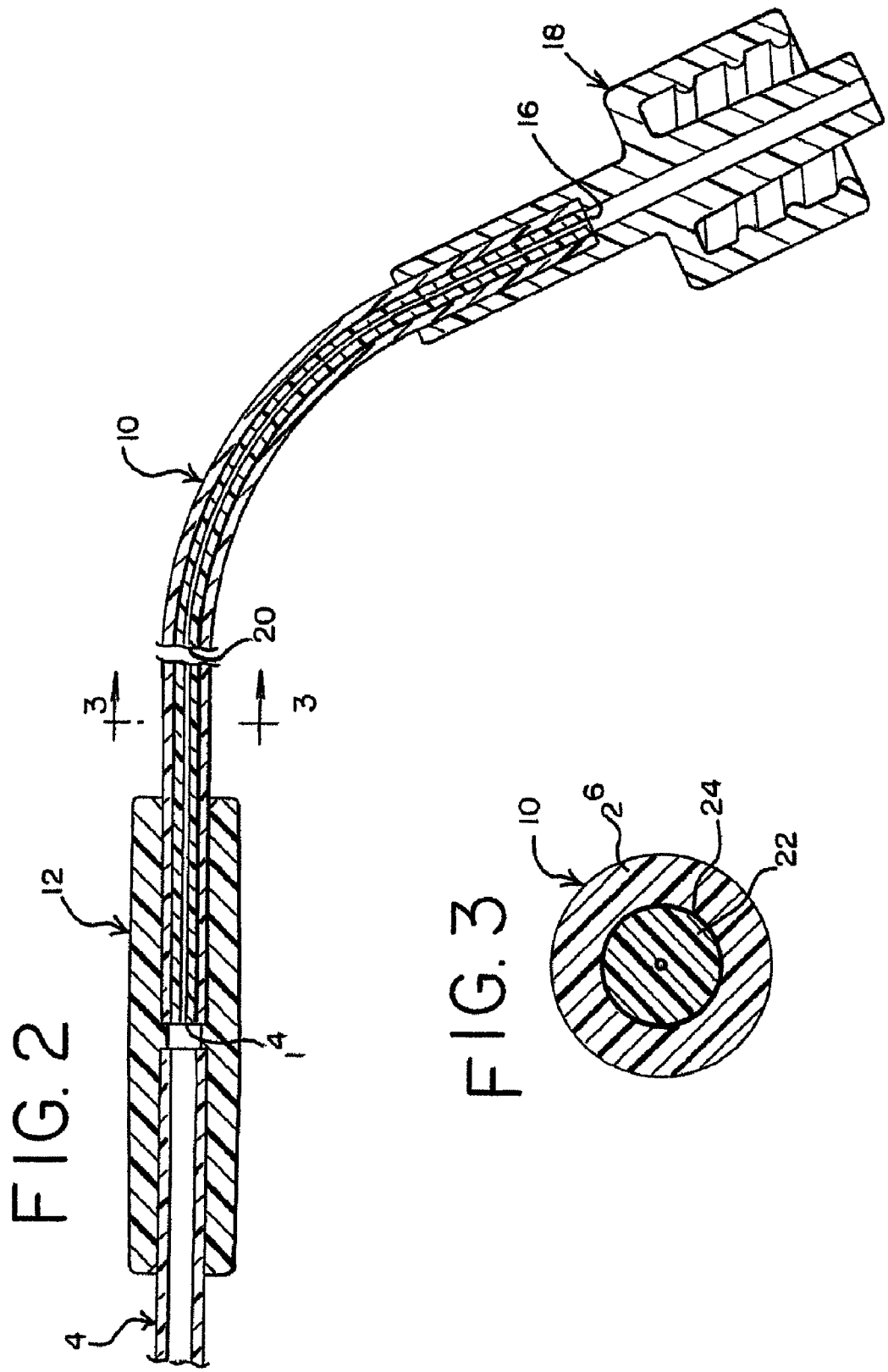

FLOW RESTRICTOR FOR INFUSION SYSTEM

BACKGROUND

The present invention generally relates to a flow restrictor for a medical fluid infusion system, and more specifically to a novel flow restrictor that reduces occlusion and is readily attached to the remainder of the infusion system.

A medical fluid infusion system typically provides a fluid flow path between a medical fluid source and a patient. A flow restrictor may be employed along the length of such flow path to limit or control fluid flow to the patient to avoid run away flow conditions and better assure fluid flow rates in accordance with a desired fluid therapy or protocol.

Among the drawbacks of prior art flow restrictors is their tendency to occlude, reducing the flow rate therethrough. Specifically, prior flow restrictors have allowed a significant amount of vapor, such as water vapor, to evaporate from the fluid flowing through the flow restrictor. As a result, the fluid within the flow restrictor may tend to crystallize during extended storage, thereby limiting or occluding fluid flow within the flow restrictor.

While certain materials are known to limit or prevent vapor transmission, such materials commonly have other drawbacks. For example, such material are often incompatible with the other materials of the fluid flow path, in that they cannot be reliably bonded or sealed together, with the potential for fluid leakage. Also, such materials may be subject to kinking when bent, which may impede fluid delivery to the patient.

Accordingly, it is realized that there are still unmet needs for a flow restrictor in infusion systems and it is desired to provide a flow restrictor that addresses one or more of these or other shortcomings as described below.

SUMMARY OF THE INVENTION

In one aspect of the present invention, a disposable flow path may be provided for an infusion system for communication between a fluid source and a patient. The flow path includes a flow restrictor having first and second ends and defining a flow path between the ends. The flow restrictor comprises a plurality of materials, including a first material defining the flow path, which is substantially resistant to vapor transmission. The flow restrictor further comprises a second material, different than the first material, defining at least a portion of an outer surface of the flow restrictor and suitable for joining to other portions of the flow path.

In another aspect of the present invention, a disposable flow path may be provided for an infusion system for communication between a fluid source and a patient, which flow path includes a flow restrictor that defines a reduced flow area in the flow path relative to other portions of flow path located upstream or downstream of the flow restrictor. The flow restrictor in this aspect of the invention has a plurality of layers and specifically includes an inner layer that is substantially resistant to vapor transmission, and an outer layer of a material suitable for joining the flow restrictor to the other portions of the flow path for providing fluid flow between the source and the patient.

BRIEF DESCRIPTION OF THE DRAWINGS

FIG. 2 is a longitudinal cross sectional view of the flow restrictor of FIG. 1 taken along line 2-2.

FIG. 3 is a lateral cross sectional view across the diameter of the flow restrictor of FIG. 2, taken along line 3-3.

DESCRIPTION OF THE PREFERRED EMBODIMENTS

Figure 1:
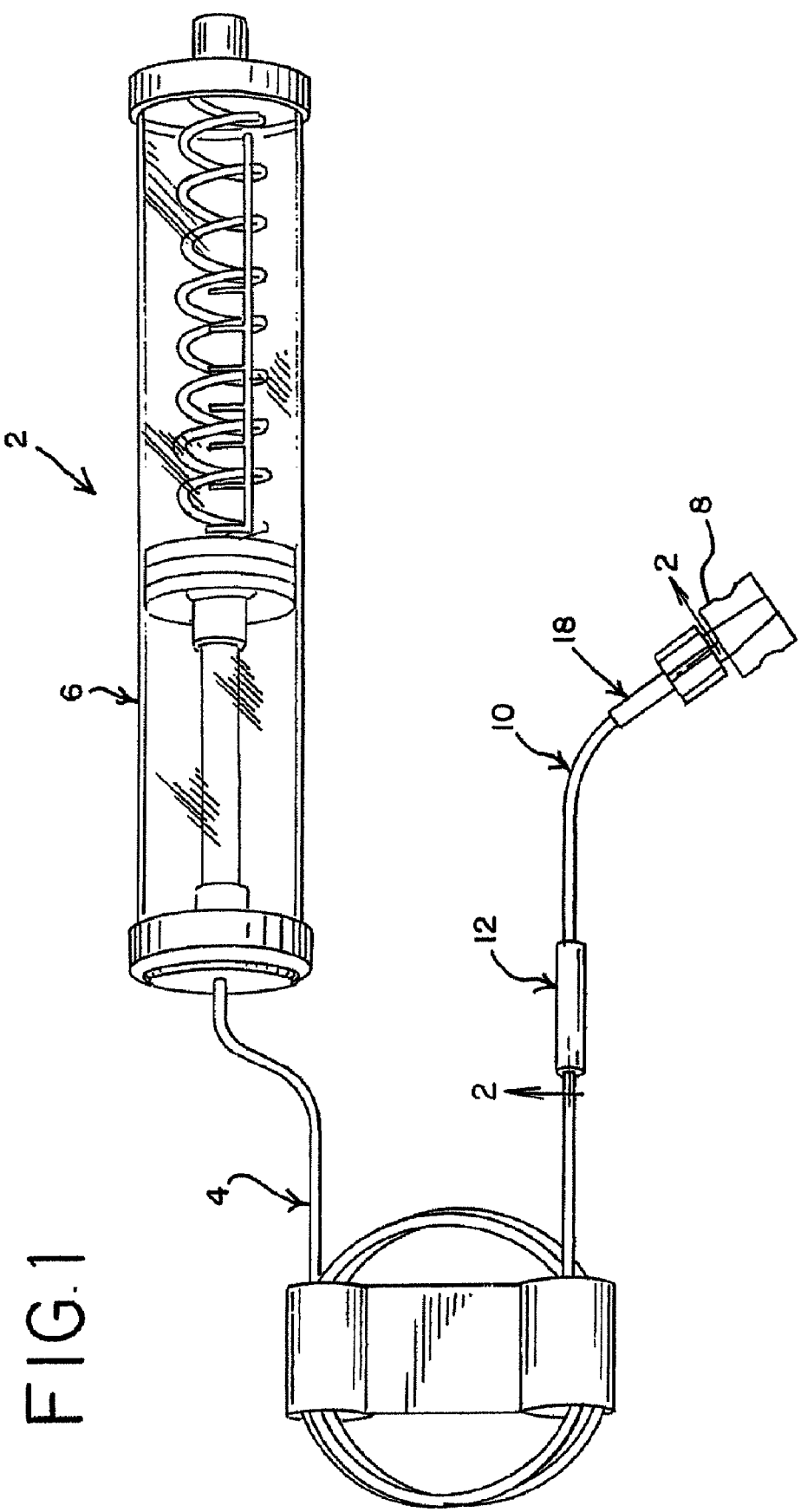
FIG. 1 is a perspective view of one example of a medical fluid administration or infusion set employing a flow restrictor of the present invention, and including a fluid source and an infusion flow path directed for delivering fluid from the source to a patient.

While the present invention will be described in terms of certain preferred or alternative embodiments for purpose of illustration, it is contemplated that the present invention may employ various structures, modifications and alternatives without departing from the scope of the invention as set forth in the claims now or hereinafter filed.

In accordance with one embodiment of the present invention, FIG. 1 illustrates a medical fluid delivery or administration system or infusion system, generally at 2, embodying the present invention. The illustrated fluid delivery system 2 is an ambulatory system for mobile or ambulatory patients. However, this is for exemplary purposes only, and the present invention is not limited to ambulatory fluid delivery systems and may be equally applied to any other medical fluid infusion systems for patients that are bedfast or otherwise non-ambulatory. In FIG. 1, the system 2 includes tubing 4 which defines a fluid flow path communicating between a fluid source, generally indicated at 6, and the patient (not shown). For attachment to a patient, the illustrated system includes a needle, needleless cannula or male luer connector generally indicated at 8, although any other patient access device such as a needle or catheter may also be employed.

The fluid source 6 may be any suitable source of medical fluid such as medicament, I.V. solution, or combination. The fluid source may include an infuser pump, such as an expandable bladder type pump, which increases in volume and pressure as fluid is introduced therein and subsequently contracts to force fluid out of the bladder during fluid delivery. Alternatively, the fluid source 6 may be a fluid container that provides fluid flow due to gravity such as, for example, by locating the fluid source at a height above the entry site to the patient, where the pressure head from the column of fluid above the entry site is sufficient to provide fluid flow to the patient. Other fluid sources may also be employed and are not limited to the above described sources.

In accordance with the present invention, the illustrated ambulatory fluid delivery system in FIG. 1 includes a flow restrictor, generally indicated at 10, which limits or controls fluid flow for preventing free flow of fluid to the patient. The flow restrictor of the present invention may take any of different suitable forms. As illustrated, the flow restrictor 10 defines a length of tubing extending between a connector, generally indicated at 12, at the upstream end 14 of the flow restrictor 10 and an adaptor, generally indicated at 18, at the downstream end 16 of the flow restrictor, which may connect to the patient access device 8.

As shown in FIGS. 2-3, the illustrated flow restrictor comprises a composite construction with at least two different materials, and defines a portion 20 of the fluid flow path between the fluid source 6 and the patient. The flow path 20 through the flow restrictor has a reduced cross sectional area relative to the other portions of the flow path 4 upstream or downstream of the flow restrictor so as to limit or control fluid flow to the patient.

The flow path is preferably defined by an inner material or layer 22 that is substantially resistant to vapor transmission.

However, such material often is difficult to bond or seal to the other portions of the flow path 4, such as polyvinyl chloride ("PVC") or polycarbonate. For joining or bonding to the rest of the flow path or conduit, the flow restrictor includes a second material or layer 26, different from the first material 22, which is more easily joined or bonded to the other parts of the flow path. The second material may preferably define at least a portion of the outer surface of the flow restrictor for contact and bonding with upstream and or downstream components of the flow path.

FIGS. 2 and 3 illustrate one particular and preferred, but optional, form of the flow restrictor 10 of the present invention. As shown in FIGS. 2-3, the illustrated flow restrictor 10 is comprised of three materials or layers. By way of example and not limitation, the inner or first layer, generally indicated at 22, a second or outer layer, generally indicated at 26 and third intermediate layer, generally indicted at 24. It is contemplated that any number of material or layers may be used and that the layers do not necessarily have to be co-extensive. For example, it is possible for alternative constructions to include inner and outer layers with any number of intermediate layers disposed therebetween or with no intermediate layer. In the illustrated flow restrictor, each layer may have a generally tubular or cylindrical configuration, which are coaxial and extend along the length of the flow restrictor, although other configurations, orientations, extents and shapes are also possible. In addition, by way of example and not limitation, it is also possible that any one or more of the layers of the flow restrictor may not extend along the entire length of the flow restrictor and instead extend along selected one or more portions of the restrictor.

Each layer or material 22, 24, 26 of the illustrated flow restrictor 10 is preferably different from each other and preferably suited to providing desired characteristics for such layer. The first or inner layer or material 22 preferably is substantially resistant to vapor transmission, more preferably water vapor transmission, across its thickness or radial distance so as to help maintain the concentration of fluid within the flow path and/or to limit fluid crystallization inside the flow path 20. Such material is preferably substantially inert, non-toxic and biocompatible, and has minimal impact on the fluid and/or on chemical reactions within such fluid. By way or example and not limitation, such material 22 may be comprised of a polyethylene material, preferably low density polyethylene ("LDPE"). Other materials are also possible. Preferably the material 22 has a water vapor transmission rate less than about 1.5 g/100 square inch per day (at 23° C. and 50% relative humidity) and more preferably less than about 1.2 g/100 square inch per day (at 23° C. and 50% relative humidity).

In a preferred embodiment the inner layer comprises LDPE 18DOA from Eastman. The WVTR of the inner layer carries a specification of 1.2 g/100 square inch per day (at 23° C. and 50% relative humidity) per ESTM F 372 test method.

In the illustrated flow restrictor, the third layer or material 24 is preferably made of a material that is particularly suited to placement between the first and second layers 22, 26. Such material is preferably selected to adhere, bond, fixate or attach to each of the layers 22, 26 so as to avoid leakage of fluid between the layers 22, 24, 26 that may alter the intended fluid flow rate through the flow restrictor 10. By way of example and not limitation, the third layer 24 may be made of ethylene vinyl acetate ("EVA"), which is suitable to create a bond between a first layer 22 made of LDPE and a third layer 26 made of PVC. Other suitable materials or bonding agents are also possible. Further, in the event a suitable mechanical bond can be provided between the inner and outer layers 22 and 26, the intermediate layer may be eliminated in whole or in part.

In the illustrated restrictor, the outer or second layer 26 is preferably made of a material that provides for ease of direct bonding or connection with each of the connector 12 and the adaptor 18, as shown in FIG. 2. By way of example and not limitation, the connector 12 and adaptor 18 may be made of polycarbonate material, which is readily solvent bondable to PVC, one of the preferred materials for the second or outer layer 26. The connector and adapter, as illustrated, each have a port or channel for receiving one end of the flow restrictor so that the outer layer of the flow restrictor is in face to face contact with the connector and adaptor, enabling secure solvent or other bonding between them.

The flow restrictor may be designed or adapted with dimensions for a desired fluid flow therapy. For a disposable ambulatory infusion therapy, an example of an outer diameter of the flow restrictor 10 may range from about 0.090 inches to 0.100 inches, preferably about 0.093 inches to 0.097 inches, more preferably about 0.095 inches. An example of an inner diameter for the flow restrictor may range from about 0.0019 to 0.0047 inches, preferably about 0.0021 inches to 0.0045 inches, although the inner diameter will vary according to the desired target flow rate. The length of the flow restrictor may range from about 2 inches to 6 inches although the length will also vary according to the target flow rate, with a longer flow restrictor creating more resistance to fluid flow therethrough. For example, a desired or target flow rate may typically range from about 0.5 milliliters per hour to about 12 milliliters per hour for a disposable ambulatory infusion therapy. The higher flow rates allow the restrictor to replace rigid capillaries where parallel combinations of such capillaries were required to achieve these flow rates.

As shown in FIGS. 2-3, the different materials of the flow restrictor 10 may vary in their thickness relative to one another. By way of example and not limitation, the illustrated inner and outer layers 22, 26 may be greater in radical thickness or than the intermediate layer 24 that may be used to connect therebetween. In such example, each of inner and outer layers 22, 26 may each comprise about 47-48%, preferably about 47.5%, of the radial thickness of the flow restrictor wall. The intermediate layer 24 may have a relative percentage thickness of about 5%. Other relative thicknesses and combination of such thicknesses are also possible and not limited to the illustrated embodiment.

The flow restrictor of the present invention may be manufactured by extrusion methods. For example, the flow restrictor may be extruded over a wire that is coated with a material that eases post extrusion removal of the wire. For example, the materials 22, 24, 26 may be co-extruded over a wire coated with Teflon or another material. After extrusion, the outer surface of the tubing may be scored for extracting the wire using an automated process or machine. The tubing may then be cut with a cutting instrument to a predetermined length. Preferably, the tubing is measured and tested for desired air flow characteristics based on acceptable standards or limits. If the tubing measures within acceptable air flow limits, then the flow restrictor may be used for the desired flow therapy.

In another preferred method the tubing is cut to the desired length by an iterative process whereby the length is cut and tested, then in dependence on the test a second cut is made to trim to the desired flow rate. It is also envisioned that there may be several iterations of testing and trimming for the more exacting flow rate specifications. Other methods of manufacture are also possible and not limited to the above-described method.

As can be seen from the above description, the present invention has several different aspects, which are not limited to the specific structure shown in the attached drawings and which do not necessarily need to be used together. Variations of these concepts or structures may be embodied in other structures for carrying out delivery of medical fluids or other fluids without departing from the present invention as set forth in the appended claims.

The invention claimed is:

1. A disposable flow path for an infusion system for communication between a fluid source and a patient, the flow path comprising:
  a flow restrictor having a plurality of layers, the flow restrictor defining a reduced flow area in the flow path relative to other portions of the flow path located upstream or downstream of the flow restrictor, the flow restrictor having an inner diameter and length sized to achieve a desired fluid flow rate;
  an inner layer being substantially resistant to vapor transmission;
  an outer layer of a material suitable for joining the flow restrictor to the other portions of the flow path for providing fluid flow between the source and the patient.

2. The flow path of claim 1 further comprising an intermediate layer being disposed outwardly of the inner layer for bonding the inner and outer layers together.

3. The flow path of claim 1 wherein the inner layer is substantially resistant to water vapor transmission.

4. The flow path of claim 1 wherein the inner layer is made of low density polyethylene LDPE.

5. The flow path of claim 2 wherein the intermediate layer is disposed radially between the inner and outer layers.

6. The flow path of claim 2 wherein the intermediate layer is made of ethylene-vinyl acetate EVA.

7. The flow path of claim 1 wherein the outer layer is made of polyvinyl chloride PVC.

8. The flow path of claim 1 wherein the flow restrictor includes an inner diameter within the range of about 0.0020 inches to 0.0045 inches.

9. The flow path of claim 1 wherein the flow restrictor includes a length within the range of about 2 inches to 6 inches.

10. The flow path of claim 2 wherein the radial thickness of the inner and outer layers are greater than the radial thickness of the intermediate layer.

11. The flow path of claim 2 wherein the ratio of radial thickness between the inner layer and intermediate layer is about 9.5 to 1.

* * * * *